United States Patent
Rabinovitch et al.

(10) Patent No.: US 6,463,330 B1
(45) Date of Patent: Oct. 8, 2002

(54) METHOD AND DEVICE FOR THE CANCELLATION OF UNWANTED EXCITATION WAVES IN THE HEART

(75) Inventors: Avinoam Rabinovitch, Omer; Eli Ovsyshcher, Beer-Sheva, both of (IL)

(73) Assignee: Ben-Gurion University of the Negev, Beer-Sheva (IL)

( * ) Notice: Subject to any disclaimer, the term of this patent is extended or adjusted under 35 U.S.C. 154(b) by 0 days.

(21) Appl. No.: 09/415,118

(22) Filed: Oct. 8, 1999

(30) Foreign Application Priority Data

Sep. 23, 1999 (IL) .................................................. 132036

(51) Int. Cl.$^7$ .............................. A61N 1/36; A61N 1/39; A61N 1/32
(52) U.S. Cl. ............................................ 607/67; 607/5
(58) Field of Search ............................ 607/2, 14, 15, 607/66, 67, 70, 72, 74, 5

(56) References Cited

U.S. PATENT DOCUMENTS

| | | | | |
|---|---|---|---|---|
| 3,895,639 A | * | 7/1975 | Rodler | 607/67 |
| 4,559,946 A | * | 12/1985 | Mower | 607/5 |
| 5,873,896 A | * | 2/1999 | Ideker | 607/14 |
| 6,240,314 B1 | * | 5/2001 | Plicchi et al. | 607/14 |
| 6,317,631 B1 | * | 11/2001 | Ben-Haim et al. | 607/9 |

* cited by examiner

Primary Examiner—Carl Layno
(74) Attorney, Agent, or Firm—Merchant & Gould P.C.

(57) ABSTRACT

A device for canceling unwanted excitation waves in an excitable tissue, particularly those causing cardiac tachyarrhythmias, which comprises circuitry for generating a unidirectional Device-Generated Excitation Wave (DGEW) in the tissue. The device comprises first and second stimulation electrodes, each fed by a power supply, which generate current impulses having magnitudes respectively lower and higher than the threshold level of the excitable tissue. The positions and activation timing of the electrodes are set so that the two impulses interact with each other only in one desired direction and every impulse except the desired DGEW decays. A method is also provided for suppressing malignant cardiac arrhythmias, caused by an unwanted excitation wave, which comprises generating in two different locations of the myocardium two excitation impulses having magnitudes respectively lower and higher than the threshold level of the excitable tissue, determining the distance between said locations and the time of the generation of the impulses so that a unidirectional DGEW is generated, and applying the DGEW to the myocardial tissue to cancel the uwanted excitation wave in its re-entry path.

57 Claims, 13 Drawing Sheets

0
METHOD AND DEVICE FOR THE CANCELLATION OF UNWANTED EXCITATION WAVES IN THE HEART

FIELD OF THE INVENTION

The present invention relates to a device for controlling the electrical activity of the heart. More particularly, the invention relates to a device and a method for the cessation and/or prevention of malignant cardiac arrhythmias.

BACKGROUND OF THE INVENTION

Sudden cardiac death is heralded by the abrupt loss of consciousness within a short period of time (usually not more than one hour) after the onset of acute symptoms. Estimates indicate nearly 400,000 sudden cardiac deaths annually for the USA only. Malignant cardiac arrhythmias such as Ventricular Tachycardia (VT) and Ventricular Fibrillation/Flutter (VF) are included in one category that is a major cause of sudden death usually associated with a diseased human heart. When VT/VF occurs, the patient may die within a few minutes without immediate intensive care. The conventional treatment which is normally given to the patient in the hospital is delivering a high energy electrical shock to the heart, usually from 200–400 Joules (J). The shock is applied between two electrodes (paddles) of an external defibrillator attached to the patient's chest. This shock resets the electrical activity of the heart, so as to enable a new natural initiation of normal electrical activity. However, these relatively high energy levels may cause heart tissue damage, especially in cases of multiple shocks, and in the long run may be dangerous, particularly in patients with a diseased heart. In addition, due to the severe pain caused by high energy impulses plus possible harm by severe contraction of the body musculature, high energy cardiac shocks are usually administered to unconscious or anesthetized patients.

The most effective method for appropriate management of patients who suffer from VT/VF is by employing an implantable cardiovertor defibrillator (ICD) device. This ICD applies electrical shocks directly to the heart when the device itself diagnoses VT/VF. These directly applied shocks are of much lower energy than those of the external defibrillator (normally ranging between 10 and 30 J), but, even this relatively low-energy application is very painful and may be harmful to the heart muscle in the long run.

Normal heart activity is controlled by impulses, which are generated at the sino-atrial node, and propagate from cell to cell through the special conduction system and myocardium, thereby causing an ordered contraction. Excitation in normal heart tissue is followed and terminated by refractoriness. This important feature of the heart provides it with electrical stability, so that abnormal excitation waves cannot propagate during the refractory period.

The exact mechanisms of malignant cardiac arrhythmias are not completely clear. In most cases it is assumed that they result from a "source" in the heart, around which a closed electrical circuit is generated, thereby forming a "reentry" path in the myocardium. There are two main approaches for management of malignant cardiac arrhythmia: pharmacological and non-pharmacological. The former generally can prevent and treat malignant cardiac arrhythmias, however its clinical effect for preventing sudden cardiac death is relatively low. In the non-pharmacological approach, malignant arrhythmias such as VT or VF may be treated by electrical shock (defibrillation/cardioversion) and can be prevented by ablation (annihilation) of part of the re-entry pathway or of the "source" of abnormal electrical activity.

All the methods described above have not yet provided complete satisfactory solutions to the appropriate overall management of malignant cardiac arrhythmias.

It is an object of the present invention to provide a method and a device for the management of malignant cardiac arrhythmia, which overcomes the drawbacks of the prior art.

It is another object of the present invention to provide a method and a device for the management of malignant arrhythmia, using very low energy impulses.

It is still another object of the present invention to provide a method and a device for the management of malignant arrhythmia without immediate or delayed negative effects on the patient's myocardium.

It is still another object of the present invention to provide a method and a device for the management of VT/VF, the use of which is not painful.

Other objects and advantages of the invention will become apparent as the description proceeds.

SUMMARY OF THE INVENTION

While the device of the invention is designated herein as a "device for the cancellation of unwanted excitation waves", it should be understood that the "unwanted excitation waves" are those causing cardiac tachyarrhythmias, and the use of the device to prevent or terminate these waves or other related pathological phenomena is included in the invention.

The device of this invention comprises the means for canceling unwanted excitation waves that propagate in an excitable tissue, by generating an excitation wave that spreads preferentially in a desirable direction. The excitation wave, also termed Device-Generated Excitation Wave (DGEW) may be directed opposite to that of the unwanted excitation wave and could cancel it or reduce it to such a magnitude that it ceases to propagate and decays. Said means for controlling the spread of the DGEW comprises two bipolar stimulating electrodes, which are adapted to be inserted into the excitable tissue at two different locations. Each stimulation electrode is fed by a power supply. Each stimulation electrode preferably comprises a pair of conducting needles, each of which comprises a relatively sharp tip at its distal end, and the proximal end of each such needle is connected to the contact of said power supply. When in use, each needle of the pair has an opposite polarity and they form a closed conducting current path through the underlying excitable tissue. The proximal end of each opposite-polarity needle is connected to a different contact of the corresponding power supply. When reference is made herein to a first and a second power supply, one for each pair of opposite-polarity stimulation electrodes, this should be understood to signify that the means for independently feeding power to each needle pair is provided, whether through two separate power sources or through a single power source with two separately controllable outputs. The device further comprises a first and second control circuitry, respectively, for generating the required amplitude and duration of the voltage applied between the respective needles. This forces a clamped current impulse to flow between the needles of each stimulation electrode. While reference is made to a first and second control circuitry, they can and generally are included in a single electronic circuit.

The first power supply, which drives the first stimulation electrode, is set to generate a first current stimulus, $S_1$, with magnitude that is lower than the threshold level of the excitable tissue. Hereinafter, the term "threshold lever" is used to describe the current stimulus magnitude, at which the tissue becomes excited and the DGEW starts to propagate actively throughout the tissue. Stimuli below the threshold level cannot elicit an actively propagating wave along the tissue and decays over space and time. The second power supply, which drives the second stimulation electrode, is set to generate a second current stimulus, $S_2$, with magnitude that is higher than the threshold level of the excitable tissue. The terms "first and second" current stimuli do not indicate timing, but indicate that the stimuli are delivered by the first and the second stimulating electrode, respectively.

The combination of $S_1$ and $S_2$ generates a DGEW, which spreads preferentially in one direction, that is controllable and can be made to be opposing to the unwanted wave. The delay between $S_1$ and $S_2$ is set by a timing circuitry to compensate for any change in the relative location between the two stimulation electrodes that may be desired.

Preferably, the distance between the two stimulating electrodes is adjusted to be approximately between 0.1 and 1.5 mm. Preferably, the distal end of the needle of each stimulating electrode consists of a 100

82 m long exposed metal cone, with a 10 $\mu$m diameter tip. The needle segment connecting between its proximal end and its distal end is insulated, so as to limit current impulse generation to the vicinity of the distal end. Preferably, the magnitude of the second current impulse, $S_2$, is between 1.25 and 1.5 times the threshold level of the excitable tissue. Preferably, the delay between the two impulses (which is equal to timing of $S_2$ minus timing of $S_1$) is between −10 mSec and +5 mSec, and the duration of each current impulse is approximately 100 $\mu$s. The propagation direction of the remaining DGEW can be switched by increasing the magnitude of the first stimulus, $S_1$, above the threshold level of the excitable tissue, and decreasing the magnitude of the second stimulus, $S_2$, below the threshold level of the excitable tissue. The distance between the two stimulating electrodes is set so that the two impulses interact with each other only in one desired direction, while preventing interaction in the opposite direction.

Preferably, the device comprises a detector circuitry, linked to the aforesaid first and second control circuits of each stimulation electrode and to the timing circuitry, for detecting unwanted excitation waves in the excitable tissue which are above the threshold level. The device is operated automatically whenever an unwanted wave is detected. In response, an opposing impulse wave is generated. Said wave interferes with the unwanted one and reduces its magnitude below the threshold level, thereby causing the unwanted wave to decay. The device can reside outside of the excitable tissue with only the electrodes implanted within the tissue. Alternatively, the whole device can be implanted in the excitable tissue. The invention further comprises the use of the aforesaid device for suppressing malignant cardiac arrhythmias.

The present invention is also directed to a method for medical treatment and suppression of malignant cardiac arrhythmias in patients, resulting from unwanted excitation waves generated and sustained in closed re-entry conductive paths in the heart of the patient, by generating unidirectional excitation waves for interacting with the unwanted excitation waves and canceling them. The method enables medical treatment and suppression of malignant cardiac arrhythmias in patients, resulting from unwanted excitation wave. Low-energy, asymmetrical excitation impulses are generated in two different locations in the myocardium. The first impulse has a magnitude below the threshold level of the myocardium tissue, and the second impulse has magnitude above the threshold level. The distance between the two locations, and the time of the generation of the impulses is determined, so that the passive electric depolarization generated by the first excitation impulse interacts with the propagating action potential generated by the second excitation impulse, thereby preventing the spreading of excitation wave in an undesirable directions. The remaining unidirectional excitation wave cancels the unwanted wave in its re-entry path. Preferably, one excitation impulse is generated with a delay in respect to the other excitation impulse. Both excitation impulses may also be generated concurrently.

Let us call the impulses that travel in one direction "d impulses" and those that travel in the opposite direction "s impulses" and let us say that the unwanted impulse is a "d impulse". Then one applies two electrodes A and B, wherein electrode A generates two impulses Ad and As above the threshold and B generates two impulses Bd and Bs below the threshold. Impulse As will interact with the unwanted impulse and these two impulses will cancel each other. Impulse Bd will decay. The distance between the electrodes and the timing of impulse generation are either such that impulse Ad interacts with impulse Bs before this decays, and the interaction generates a residual impulse that is below the threshold and therefore decays. However, alternatively, if the two electrodes are sufficiently close to one another, no impulses are generated between them, viz. there are no impulses Ad and Bs. In either case, no impulse thus remains to propagate through the heart tissue.

Therefore, the method comprises:

a—generating, by means of a first electrode, a first impulse above the threshold that propagates opposite to the unwanted impulse, whereby when it meets said unwanted impulse, the two impulses cancel one another;

b—generating, by means of a second electrode a second impulse below the threshold, that propagates in the same direction as the unwanted impulse and decays; and c—choosing the distance between said electrodes and the timing of the impulse generation in such a way that the first electrode generates a third impulse above the threshold that propagates in a direction opposite to that of said first impulse threshold, while the second electrode generates a fourth impulse below the threshold that propagates in a direction opposite to that of said second impulse, whereby said third and fourth impulse meet and their interaction generates a residual impulse that is below the threshold and decays;

d—provided that if said distance is small enough, no third and no fourth impulse are generated.

The present invention also provides a method for localizing the pathological tissue (or pathways) that are responsible for arrhythmias. The location of the re-entry path of the unwanted excitation wave are identified from the direction of the remaining sub-impulse when this latter cancels the unwanted excitation wave, and destructive energy is delivered to the identified location.

In the following description, it is assumed that the stimulation electrodes are positive; however, this is not to be construed as an absolute, and they could be negative.

BRIEF DESCRIPTION OF THE DRAWINGS

The above and other characteristics and advantages of the invention will be better understood through the following illustrative and non-limitative detailed description of preferred embodiments thereof, with reference to the appended drawings, wherein.

DETAILED DESCRIPTION OF PREFERRED EMBODIMENTS

The functionality of excitable systems may be controlled and improved by applying electrical impulses of particular parameters at specific locations. By controlling the stimulating impulse characteristics and location, several desired responses may be obtained. One of these characteristics is the direction along which the DGEW propagates.

Figure 9:
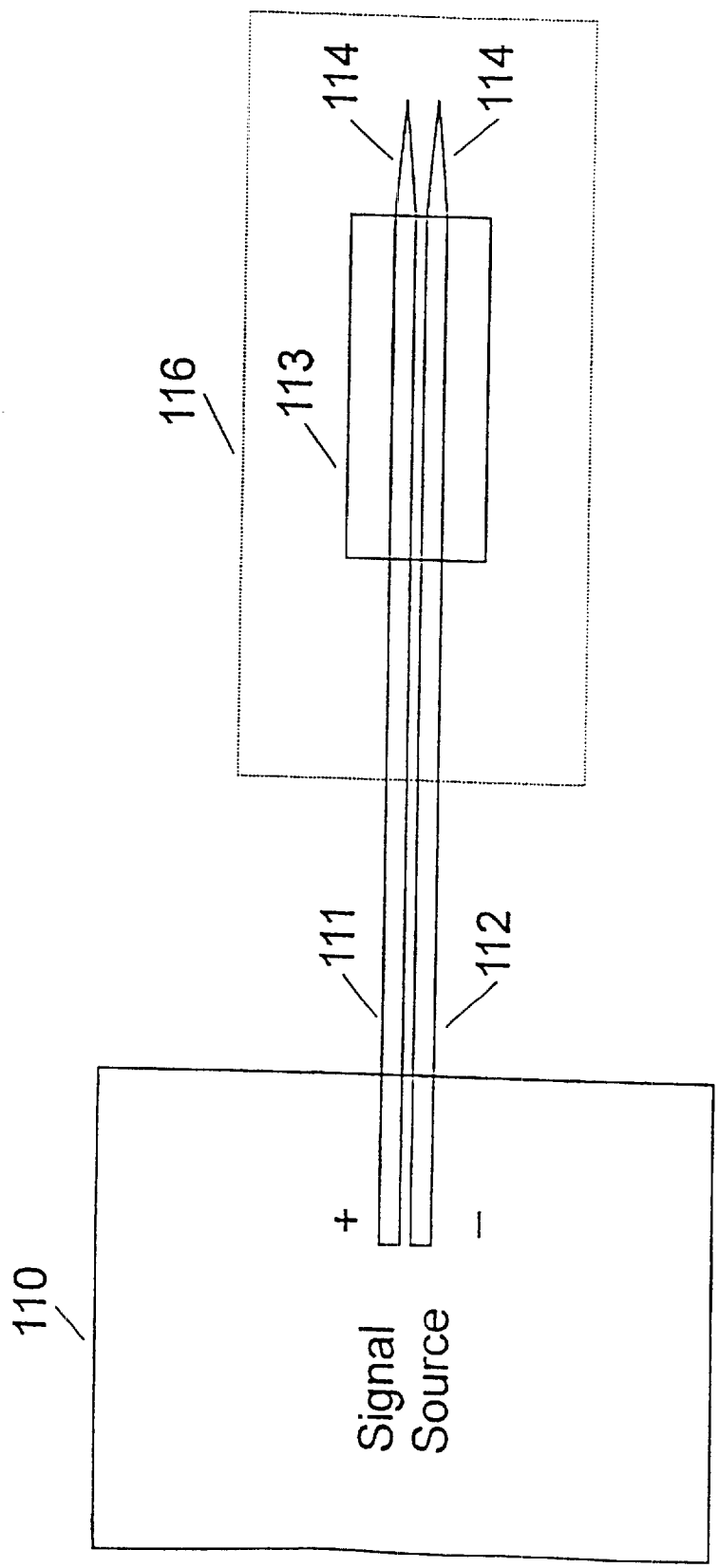
FIG. 9 schematically illustrates a typical prior art electrode arrangement for generating impulses in excitable tissues.

Generating a unidirectional DGEW in an excitable medium, such as cardiac tissue, is carried out by exploiting an electrode, which is immersed in the excitable medium and excited with electrical energy delivered from a voltage or current source. Generally, an excitable medium is able to sustain electrical DGEWs generated in response to electrical stimuli. The feasibility and the shape of the generated, unidirectional DGEW are mainly affected by the characteristics of the excitable medium, as well as the structure of the stimulating electrode. For a better understanding of the present invention, an example (prior art) of a device for generating stimuli is shown in FIG. 9. An electrical signal source 110 is connected to two insulated conductive needles 111 and 112 of the bipolar stimulating electrode 116. Every conductive needle 111 and 112 consists of a metal tip 114 at its distal end, through which an excitation impulse is delivered. The rest of the conductive needle is insulated; and the two needles are covered by the insulating sleeve 113. Electrode 116 is inserted into an excitable medium, until both the tips 114 are in electrical contact with the tissue. Since the tissue is electrically conductive, voltage applied between needles 111 and 112 causes a current to flow between tips 114, which function as the two electric contacts of the electrode 116. The current flows via the excitable medium, and its magnitude is determined by the impedance of the excitable medium and the contacts. Knowing the impedance, the current magnitude may be controlled by varying the applied voltage. Alternatively, the current can be "clamped" to a given value by usage of very low internal impedance current source. The current excites the excitable medium and a resulting response DGEW is generated.

Figure 10:
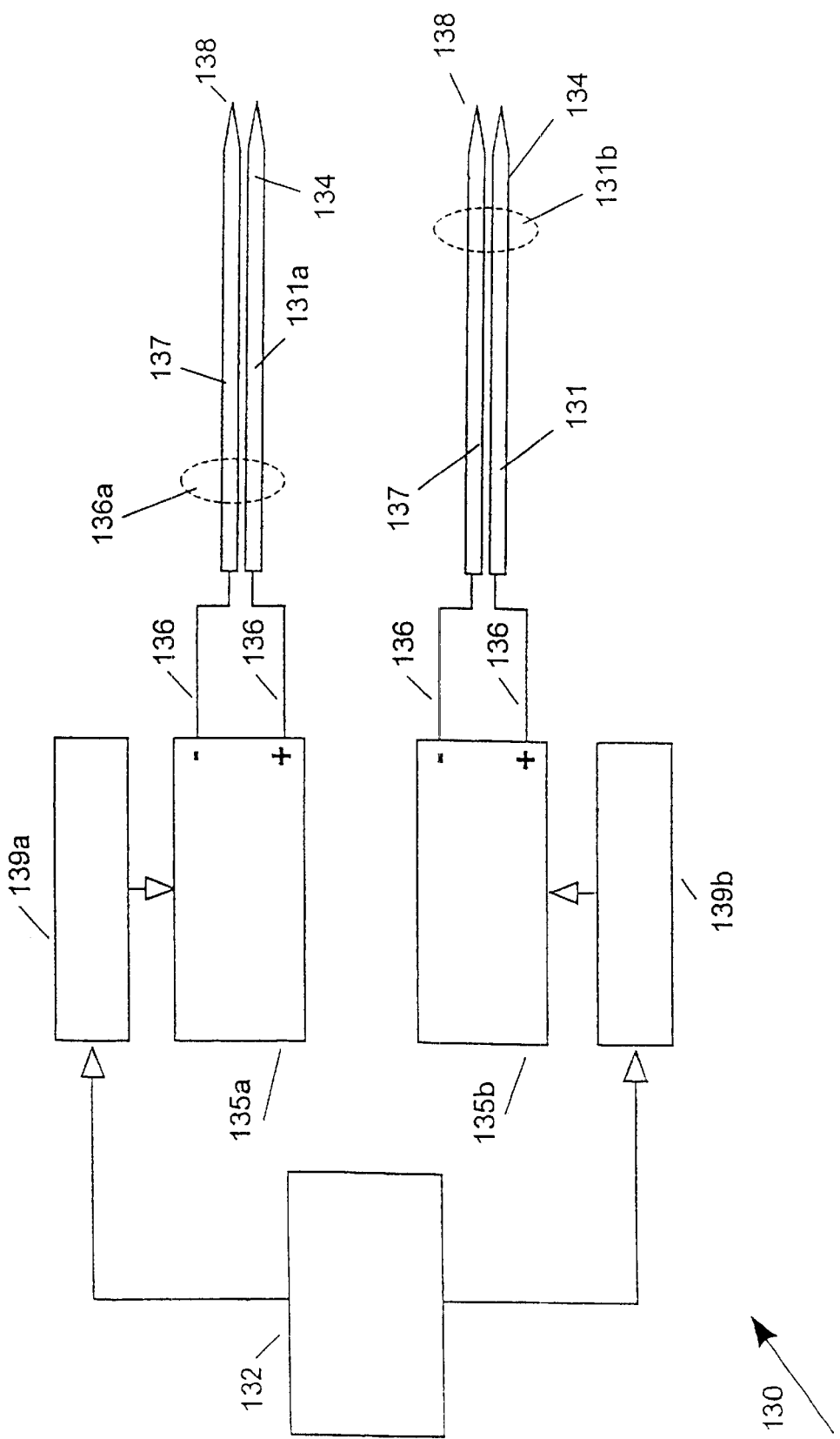
FIG. 10 schematically illustrates the structure of a device for generating unidirectional DGEWs, propagating in an excitable tissue, according to a preferred embodiment of the invention.

FIG. 10 schematically illustrates the structure of a device for generating a unidirectional DGEW, propagating in excitable tissue, according to a preferred embodiment of the invention. The device 130 comprises two positive conductive needles, 131 and 131a (shown in FIG. 11), which are inserted into the excitable tissue at two different locations. Each positive conductive needle comprises a relatively sharp tip 134 at its distal end. The proximal end of the needle is connected to the positive contact of a power supply 135 by a suitable flexible insulated wire 136. A negative conductive needle 137 forms a closed conducting current path through the excitable tissue, which is stimulated by the power supply 135. The distal end 138 of the negative needle is implanted in a predetermined location in the excitable tissue. The proximal end of the negative electrode is connected to the negative contact of the power supply 135. Each power supply 135 comprises a suitable control circuitry 139 for determining the required amplitude and duration of the voltage applied between the positive and negative electrodes, so as to force a current impulse to flow between each positive needle and its corresponding negative needle through the excitable tissue.

According to a preferred embodiment of the invention, the control circuitry of the first power supply 135a, which drives the first bipolar electrode 136a, is set to generate a first current impulse $S_1$ with a magnitude that is lower than the threshold level of the excitable tissue. The threshold level (which can be found experimentally) is the current impulse magnitude, above which the tissue is excited and the impulse continuously propagates from cell to cell, each time exciting the next cell. Impulses below the threshold level cannot cause the continuously propagating DGEW along the tissue and these decay with time. The typical value of threshold level is approximately 7 Volts or 0.5 mA for 100 sec duration impulse. $S_1$ is below the threshold level and spreads electronically along the excitable tissue in all directions. The control circuitry 139b of the second power supply 135b, which drives the second bipolar electrode 131b, is set to generate a second current impulse $S_2$ with a magnitude that is higher than the threshold level of the excitable tissue. The resulting DGEW initiates at the site where $S_2$ is located.

According to a preferred embodiment of the invention, the first and second current impulses are generated with a predetermined delay in respect to each other. The required delay is determined in combination with the distance between the two electrodes, and is set by a timing circuitry 132 which is linked to both control circuits 139a and 139b, so that the wave initiated by $S_2$ cannot propagate actively towards $S_1$ and decays with time. However, it propagates freely in other directions.

Figure 11:
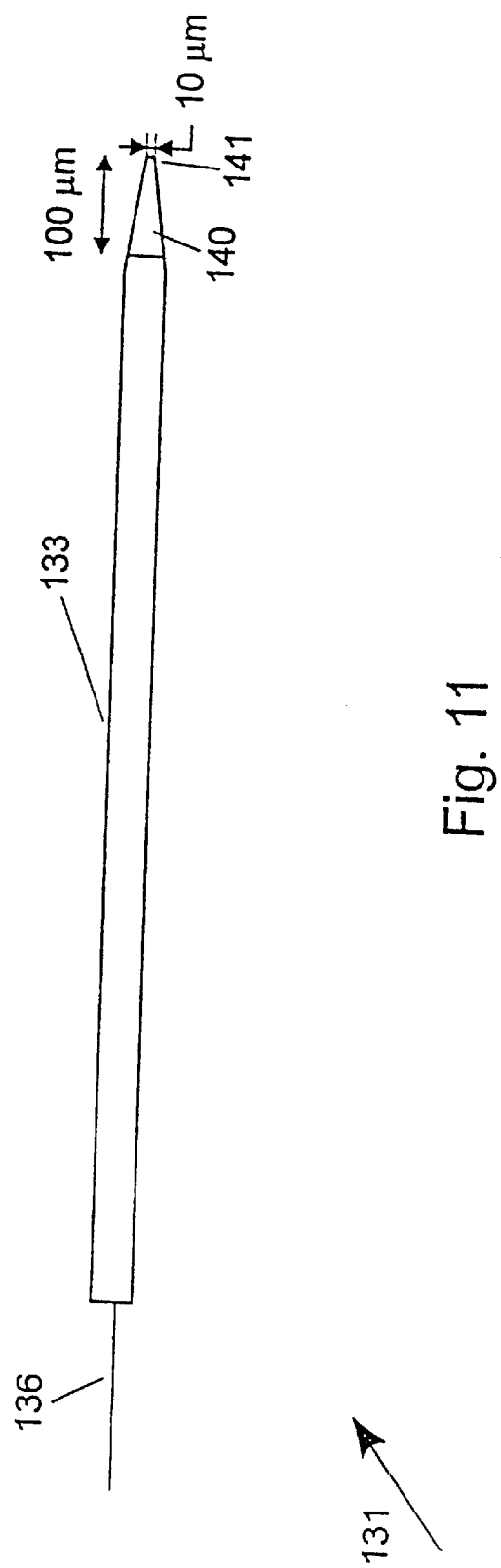
FIG. 11 schematically illustrates a typical structure of a stimulating needle, according to a preferred embodiment of the invention.

FIG. 11 schematically illustrates a typical structure of a conductive needle, according to a preferred embodiment of the invention. It consists of insulated part 133, connecting between its distal and proximal ends. The distal end consists of a 100 $\mu$m long exposed metal cone 140, ending with a 10 $\mu$m diameter tip 141. The segment 133 connecting between its proximal end and its distal end is insulated, so as to limit impulse generation to the vicinity of the distal end.

According to a preferred embodiment of the invention, the magnitude of the second current impulse provided by the second power supply 135b is set to be between 1.25 and 1.5 times the threshold level of the excitable tissue. The time delay between the two stimuli is set by the timing circuitry 132 to values between −10 and +5 mSec (relative to the supra-threshold stimulus), and the duration of each impulse is set by the control circuitry 139b to approximately 100 $\mu$sec.

Of course, the propagation direction of the DGEW created by $S_2$ can be switched by increasing the magnitude of the first impulse above the threshold level of the excitable tissue, and decreasing the magnitude of the second impulse below the threshold level of the excitable tissue.

According to a preferred embodiment of the invention, the device 130 may comprise a detector circuitry, linked to the control circuitry of each stimulating electrode and to the timing circuitry. This circuitry detects unwanted excitation waves in the excitable tissue which are above the threshold level. The detector circuitry detects unwanted waves through one or more sensing electrodes, which are implanted in predetermined locations in the excitable tissue. The device 130 is operated automatically whenever an unwanted excitation wave is detected by the detector circuitry. In response, a unidirectional DGEW of magnitude above the threshold level is generated by the device 130 and propagates in the excitable tissue. The generated unidirectional wave interferes with the unwanted wave and reduces its magnitude below the threshold level, thereby causing the unwanted excitation wave to decay. The device 130 may be located outside the excitable tissue and only the electrodes (i.e., the positive/negative and the sensing electrodes) implanted inside therein, or alternatively, the whole device 130 may be implanted in the excitable tissue. For instance, integrated circuit implementation technology can be used to obtain a miniature device.

Figure 12:
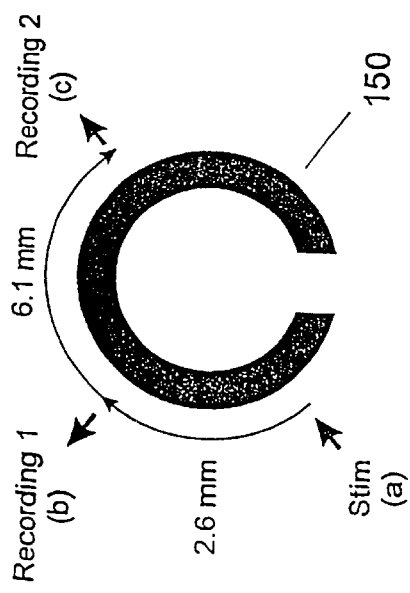
FIG. 12 schematically illustrates the recording at two different locations of a DGEW propagating in heart tissue, in response to a single stimulation.
Figure 12:
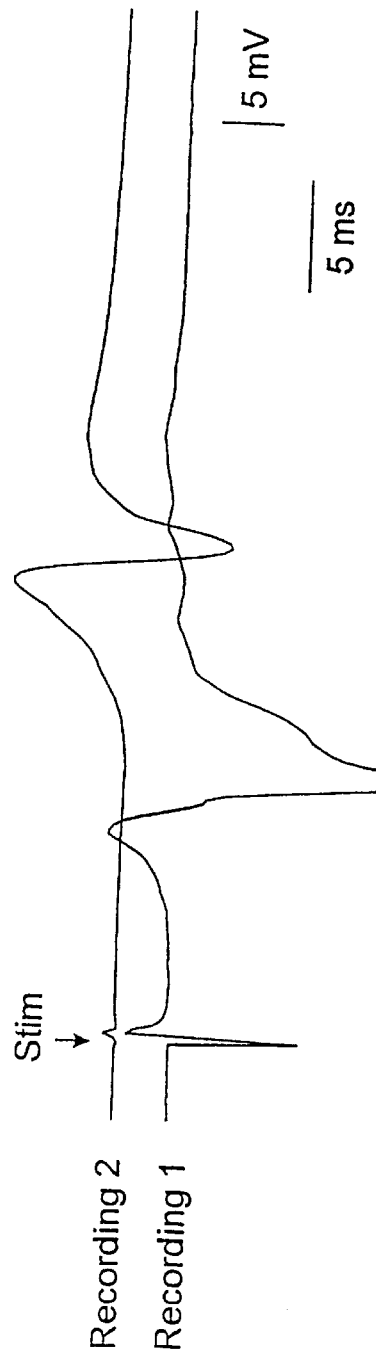

FIG. 12 schematically illustrates the recording of a DGEW propagating in the heart tissue at two different locations, in response to a single stimulus. The simulation impulse S is applied at point a in the excitable tissue 150 by a simulation electrode. The stimulation impulse S is a rectangular current impulse of 100 sec duration and approximately 10 mV amplitude (i.e., 1.5 times above the threshold level of the excitable tissue). The response DGEW propagates along the excitable tissue 150 from the stimulation point a, to the first recording point b, located 2.6 mm apart from point a, and then to the second recording point c, located 6.1 mm apart from point a. The response wave is sampled at points b and c, shown by the lower and upper traces, respectively. Both traces indicate normal propagation in clockwise direction along the excitable tissue 150.

Figure 13:
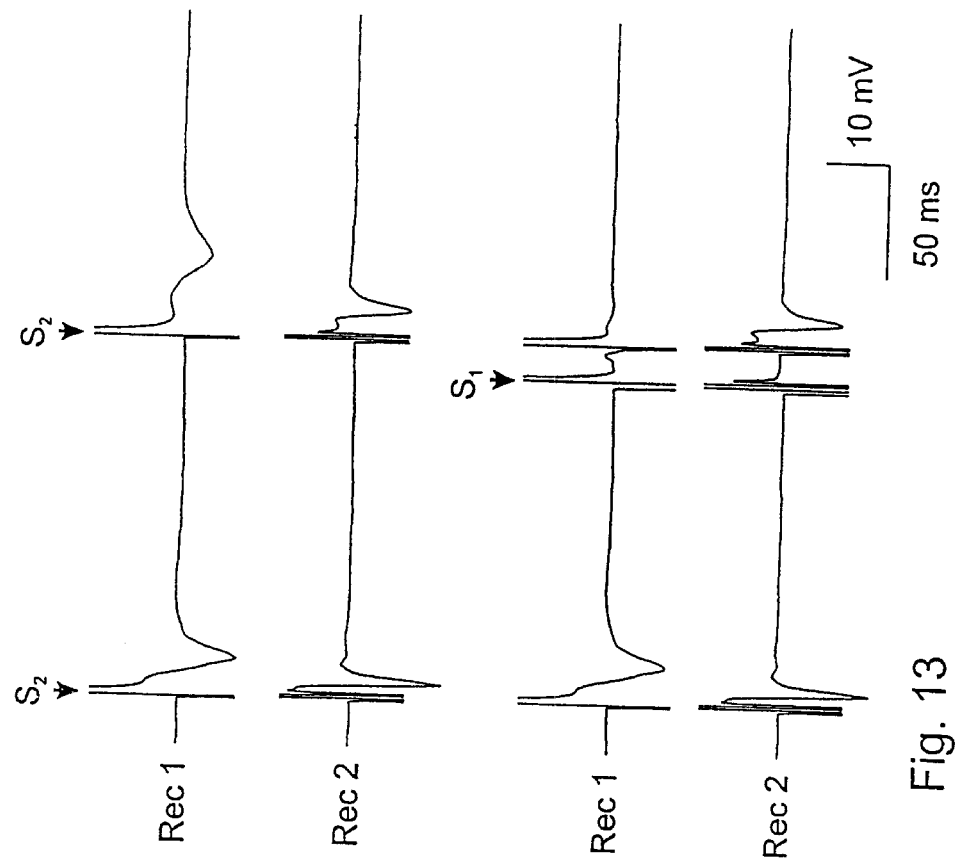
FIG. 13 schematically illustrates the generation of a unidirectional DGEW by the interference of the $S_1$ and $S_2$ stimuli, according to a preferred embodiment of the invention.
Figure 13:
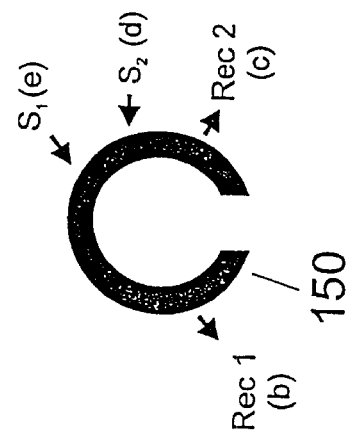

FIG. 13 schematically illustrates the generation of a unidirectional DGEW by interference of a wave propagating in one direction in an excitable tissue, in response to stimulation, and additional stimulation at a different location, according to a preferred embodiment of the invention. Two stimulation impulses, $S_1$ and $S_2$ are applied at points d and e, respectively, in the excitable tissue 150 by two simulating electrodes, located at a distance greater than 1.5 mm between them. The stimulation impulse $S_2$, which is above the threshold level, is first applied alone. The two upper traces (solid lines) show the response. The response wave is split into two similar waves: one that propagates along the excitable tissue 150 from the first stimulation point d, to the recording point b, and the other one that propagates along the excitable tissue 150 in the opposite direction from the first stimulation point d, to the other recording point c. The right "dip" in each trace indicates that the response wave propagates in the excitable tissue 150 in both directions. The stimulation impulse $S_1$, which is below the threshold level is applied at a predetermined delay, which is longer than the refractory period of the excitable tissue 150 following the first stimulation impulse $S_2$. The two lower traces (dashed lines) show the response to the first stimulation signal $S_2$ that propagates in both directions. Delivery of the second stimulation impulse $S_1$ prevents a wave initiated by the second $S_2$ to propagate in one direction. Apparently, the local electronic response to $S_1$ creates an obstacle. The result is that the impulse which has been split from $S_2$ and propagated toward point b, is canceled by $S_1$, since no "dip" in the trace recorded at point b. On the other hand, a "dip" appears in the trace recorded at point c, which indicates that there is propagation in this direction in response to $S_2$. In fact, $S_1$ "canceled" the propagation of the wave elicited by $S_2$ in one direction, and enabled the propagation of the wave elicited by $S_2$ in the opposite direction. Hence, a unidirectional impulse is obtained by setting the distance and timing of the stimuli $S_1$ and $S_2$.

According to a preferred embodiment of the invention, a unidirectional DGEW is generated by using the electrodes immersed in excitable tissue, with a specific spatially and temporary asymmetrical current application.

The generated unidirectional wave is sustained by the excitable tissue and propagates along the conduction path.

Excitable systems may be described by FitzHugh-Nagumo set of differential equations (FitzHugh-Nagumo model is disclosed, for example, in "Biological Engineering, R. FitzHuge, H. P. Schwan et al eds., McGraw Hill, N.Y. 1969"):

$$\dot{v}=D\nabla^2 \cdot v+f(v,w)+I(t,\vec{r})$$

$$\dot{w}=g(v,w)$$

wherein v represents the potential, D is the diffusion constant, w represents the refractivity and $I(t,\vec{r})$ is the input current. The functions f(v,w) and g(v,w) are given by:

$$f=v\ (v-a)(1-v)$$

$$g=c\ (v-dw)$$

wherein $\alpha$ is an excitability parameter, c represents the ratio between fast and slow time constants and d represents the resistivity of the cell. Spatial propagation basically depends on the value of the diffusion constant D and on the input current, I. In the model of a preferred embodiment of the invention, the parameters D=1 and d=3 are held constant, and all other parameters may be varied. Therefore, it is desired that the main effect will be controlled mainly by the input current. The input current is given by:

$$I(t,\vec{r})=I_1(t)\cdot I_2(\vec{r})$$

ps wherein $I_1(t)$ is a short time dependent component and $I_2(\vec{r})$ is the spatial component, which depends on the shape of the stimulating electrode. The optimal form of $I_1(t)$ has been obtained for prior art external pacing and defibrillation techniques. Therefore, in the present invention the optimal shape of $I_2(\vec{r})$ is sought. Since a symmetrical form of $I_2(\vec{r})$ leads to an (ineffective) bi-directional impulse, an asymmetrical form should be exploited to obtain the desired unidirectional DGEW.

Figure 1:
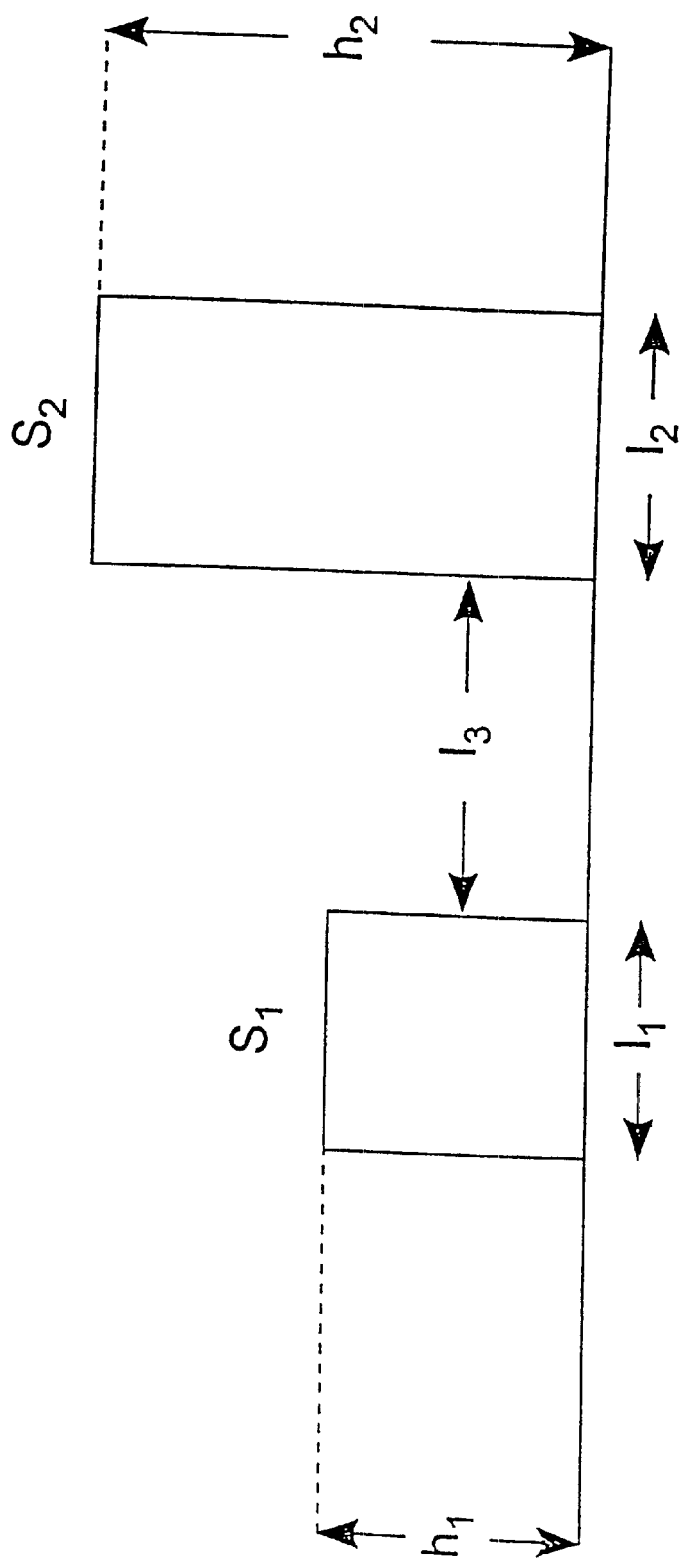
FIG. 1 schematically illustrates an asymmetrical impulse shape employed according to a preferred embodiment of the invention.
Figure 2:
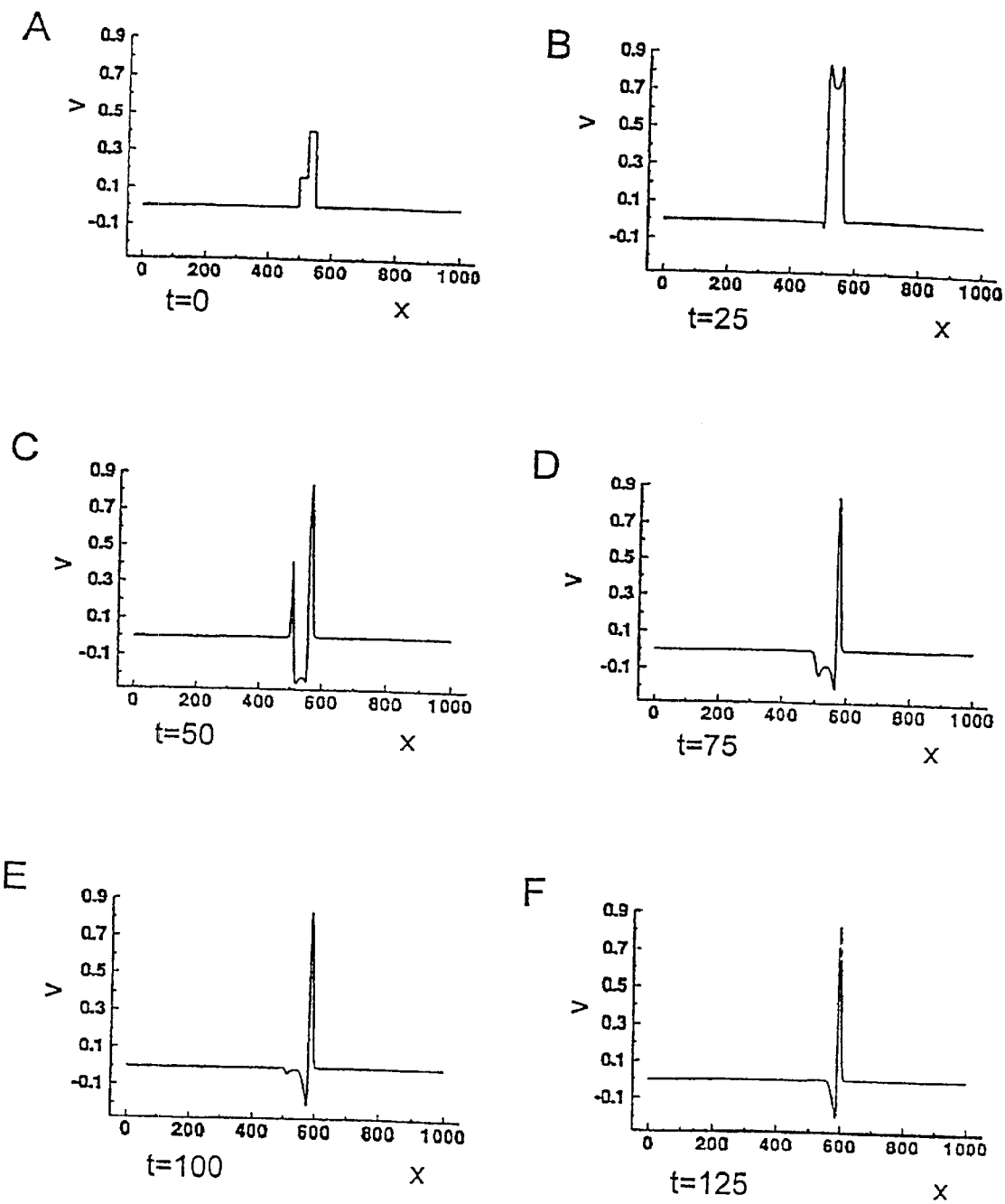
FIGS. 2A to 2F schematically illustrate the initiation and development of a one-dimensional unidirectional DGEW in response to input excitation impulses, according to a preferred embodiment of the invention.

FIG. 1 schematically illustrates an asymmetrical impulse shape $I_2(\vec{r})$ employed according to the model of a preferred embodiment of the invention. Each part of the asymmetrical input impulse (of the pair) is used to excite a corresponding contact of a dual needle electrode, with different excitation current at each needle. The magnitude and duration of each part of the asymmetrical pair, as well as the timing between $S_1$ and $S_2$, are appropriately controlled to obtain a unidirectional DGEW in response to this type of stimulation. The $S_1$ component may be a short spatial square wave or an impulse ($\delta$ function). The response wave shape depends on the magnitude of the $S_2$ component and on the ratio between the magnitudes of $S_2$ and $S_1$. Input impulses of very small magnitude will not cause any propagating wave response. Above a predetermined threshold, a unidirectional DGEW or a bi-directional wave is elicited, according to the ratio between the magnitudes of $S_1$ and $S_2$.

In the model of a preferred embodiment of the invention (FIG. 1), the input impulse consists of two square impulses, of magnitudes $h_1$ and $h_2$ and widths $l_1$ and $l_2$, respectively, spaced apart by a distance $l_3$. In the following calculation we assumed that $l_3=0$ and that $A_1=h_1 l_1 < A_{th}$, and $l_2$ may vary. According to this model of a preferred embodiment of the invention, two constants, $\alpha$ and $\beta$ which determine the response impulse resulting from an input impulse, may be defined. For an input impulse for which $0<h_2<\alpha$, no propagating response impulse is obtained. For $\alpha<h_2<\beta$, the response impulse is a unidirectional DGEW, and for $h_2>\beta$, the response impulse is a bi-directional impulse. For example, if $l_1=12$, $l_2=4$ and $h_1=0.16$, values of $\alpha=0.353$ and $\beta=0.403$. On the other hand, if $l_1=l_2=8$ and $h_1=0.16$, values of $\alpha=0.252$ and $\beta=0.262$. Therefore, the range of $h_2$ for which the response impulse is a unidirectional DGEW increases with increasing l1/l2 ratio. The required $A_1(=h_1 l_1)$ values for generating a unidirectional DGEW are smaller for $l_1/l_2=3$ than for $l_1/l_2=1$. Hence, by using asymmetrical input impulse (i.e., $l_1>l_2$), a unidirectional DGEW response is more easily obtained.

FIGS. 2A to 2F schematically illustrate the initiation and development of a one dimensional unidirectional DGEW response to a pair of input excitation impulses as a function of distance for several time points, according to the model of a preferred embodiment of the invention. At t=0, two input rectangular impulses are initiated, with almost no spacing distance ($l_3=0$).

Figure 3:
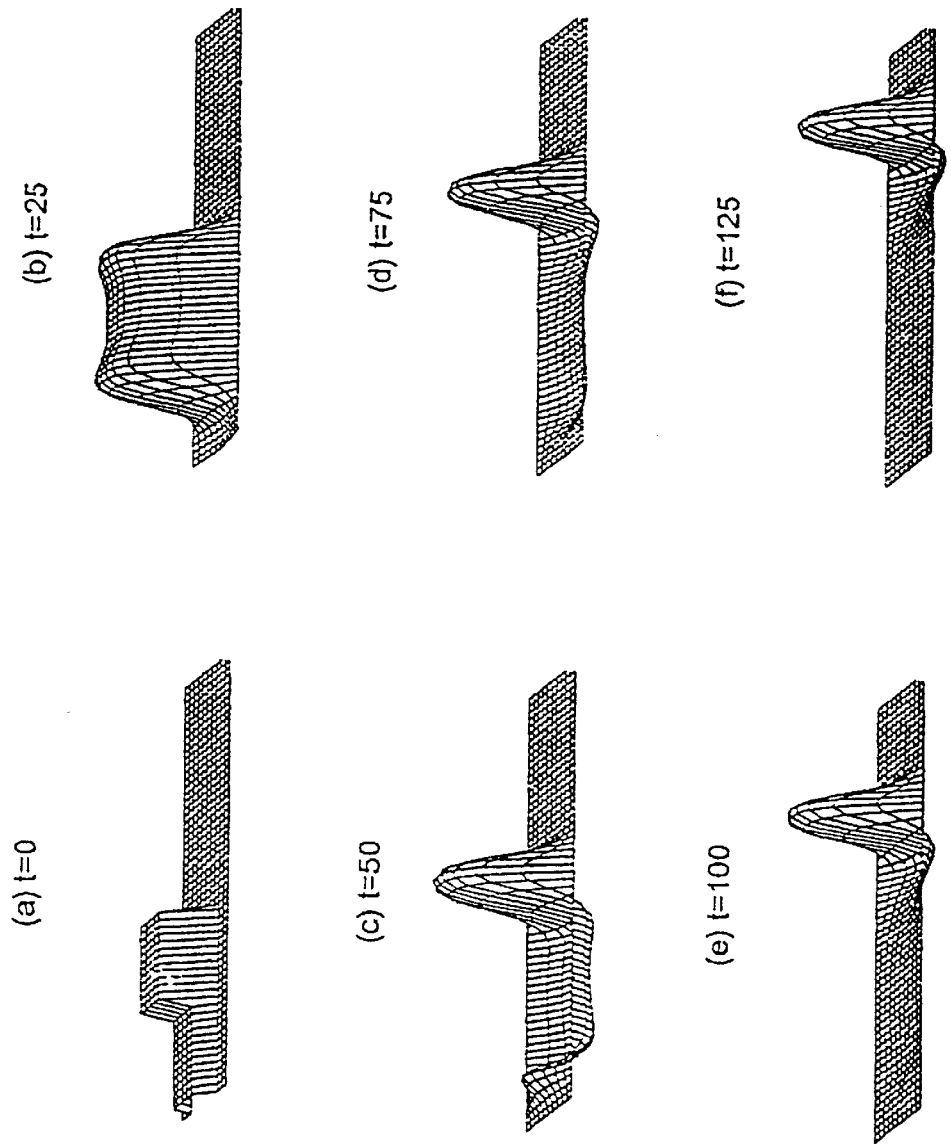
FIG. 3 is a spatial illustration of the initiation and development of a two-dimensional unidirectional DGEW propagating in a ring-type path, according to a preferred embodiment of the invention.

FIG. 3 is a spatial illustration of the initiation and development of a two dimensional unidirectional DGEW response propagating in a ring-type path, to a pair of input excitation impulses in two dimensional (x-y) plane for several time points, according to the model of a preferred embodiment of the invention. Periodic boundary conditions exist only in x direction. Finite (un-periodic) boundary conditions, v=w=0, exist in y direction. The resulting response impulse shape is a "band" in the x-y plane. The input impulse has a finite width in the y direction and asymmetrical shape in x direction. The response in the x direction is similar to the one-dimensional response of FIG. 2.

Figure 4:
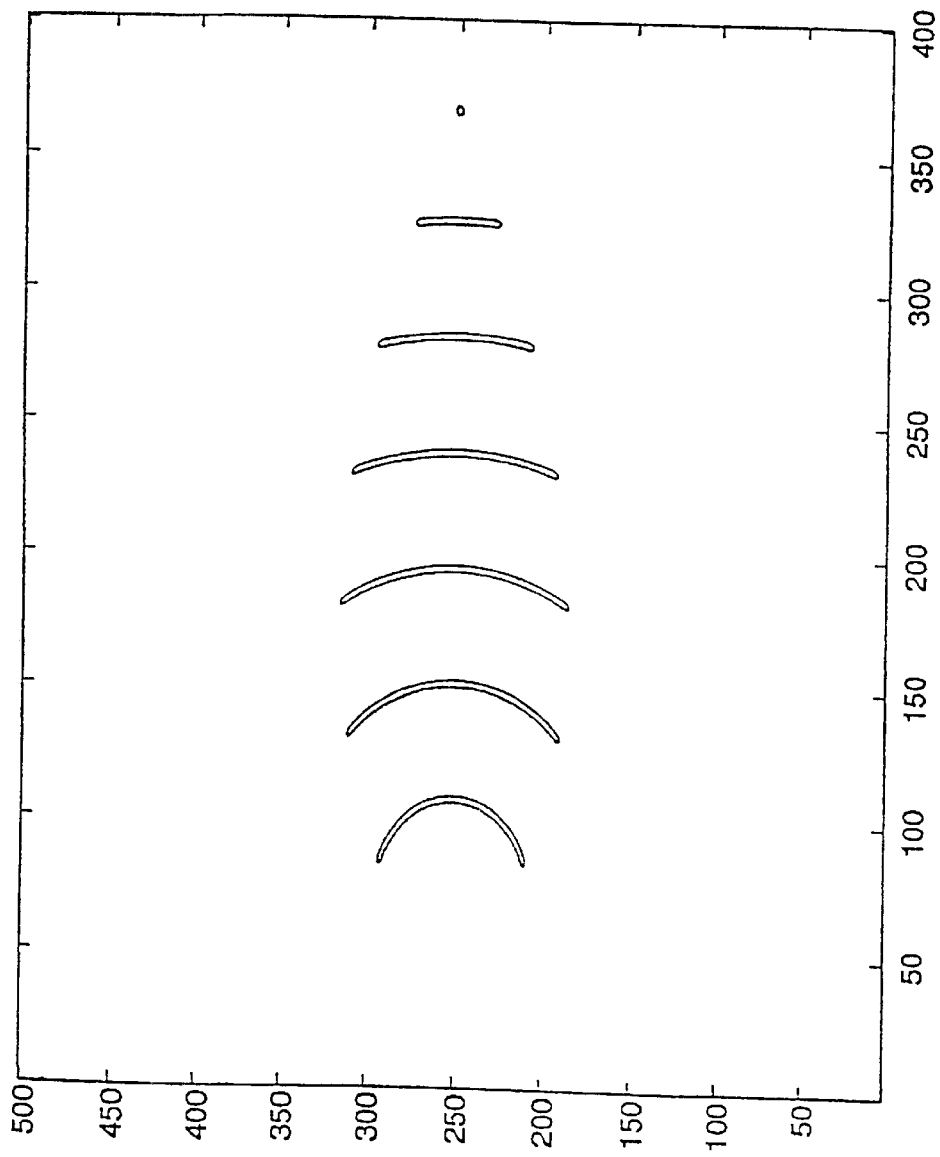
FIG. 4 schematically illustrates that in a two-dimensional excitable medium, under certain conditions, the unidirectional DGEW initiates, develops, and decays, according to a preferred embodiment of the invention.

FIG. 4 schematically illustrates the initiation, development and decay of a two-dimensional, unidirectional DGEW response propagating in a two-dimensional excitable medium, to a pair of input excitation impulses in two dimensional (x-y) plane, according to the model of a preferred embodiment of the invention. Here, the ratio c between fast and slow time constants is relatively high, and hence, unidirectional DGEWs, as well as bi-directional response waves, shrink and decay. The larger c is, the closer is the tissue to the pathological state, like ischemia (as will be described below).

Figure 5:
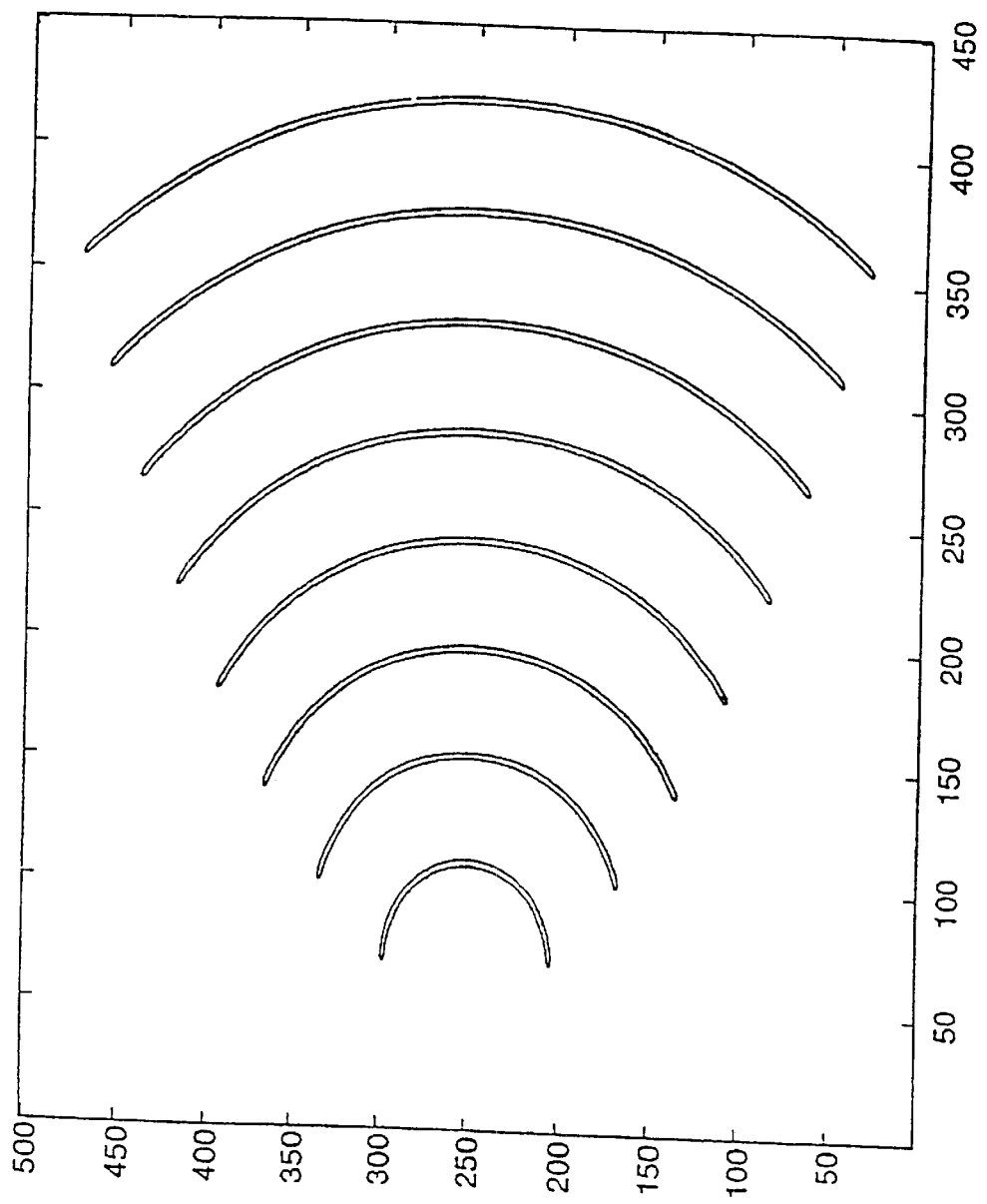
FIG. 5 schematically illustrates that, under different conditions, the unidirectional DGEW initiates, develops, and spreads, according to a preferred embodiment of the invention.

FIG. 5 schematically illustrates the initiation, development and spread of a two-dimensional, unidirectional DGEW response propagating in a two-dimensional medium, to a pair of input excitation impulses in two dimensional (x-y) plane, according to the model of a preferred embodiment of the invention. Here, tissue properties are different than those of FIG. 5. The envelope of this "plane-wave" propagating response impulse is a slowly increasing monotonic function.

Figure 6:
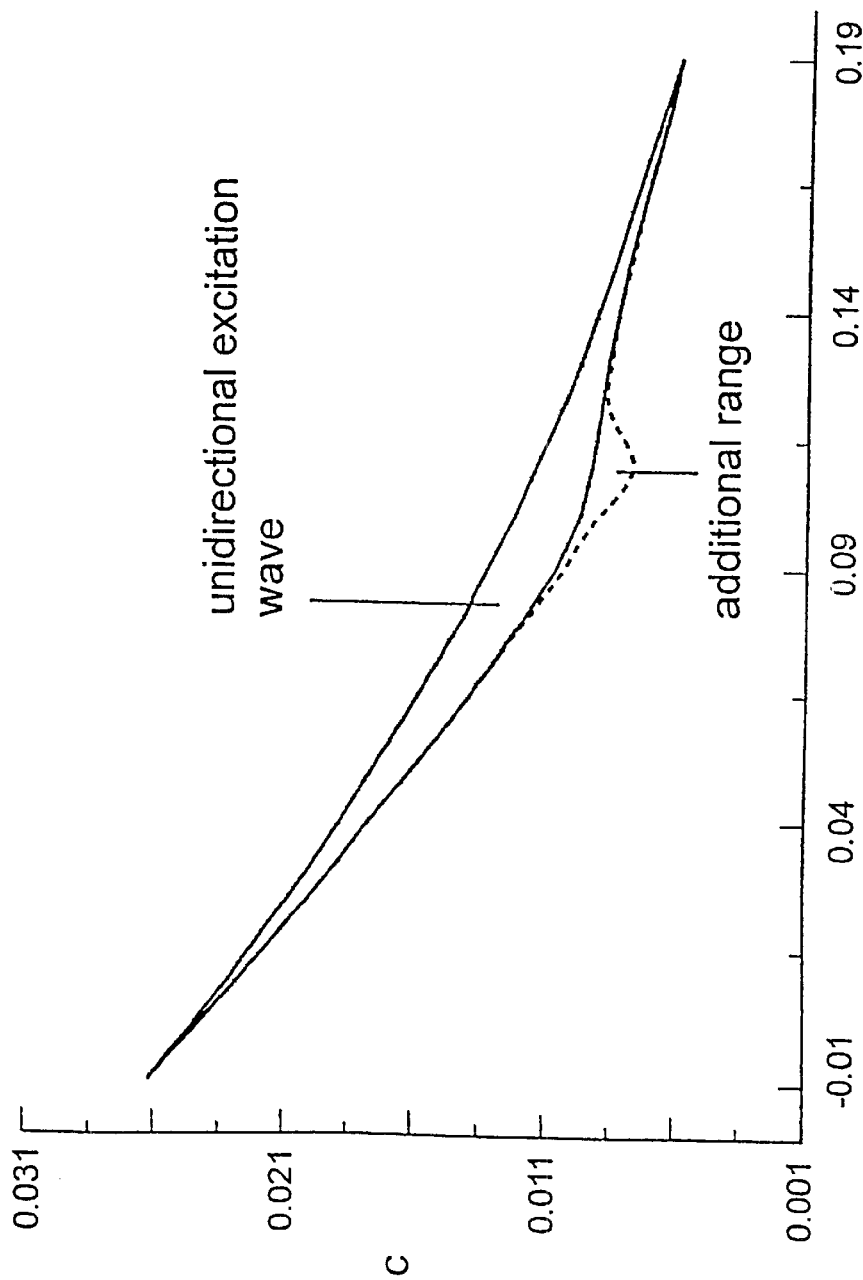
FIG. 6 schematically illustrates the range of several tissue and environmental parameters, for which a unidirectional DGEW may be obtained, according to a preferred embodiment of the invention.

FIG. 6 schematically illustrates the range of several refractory period parameters, for which a unidirectional DGEW response may be obtained, according to the model of a preferred embodiment of the invention. The unidirectional DGEW response region is plotted in the a-c plane, for fixed values of the parameters d, $h_1$ and $h_2$, and for $l_1=l_2=25$ (solid line). The upper boundary of the obtained region coincides with a portion of the boundary of the excitable region (i.e., no impulses can propagate for higher values of the parameter c). The unidirectional DGEW response region is further expanded (dashed line) by changing the values of $l_1$ and $l_2$ to 15 and 35, respectively.

Figure 7:
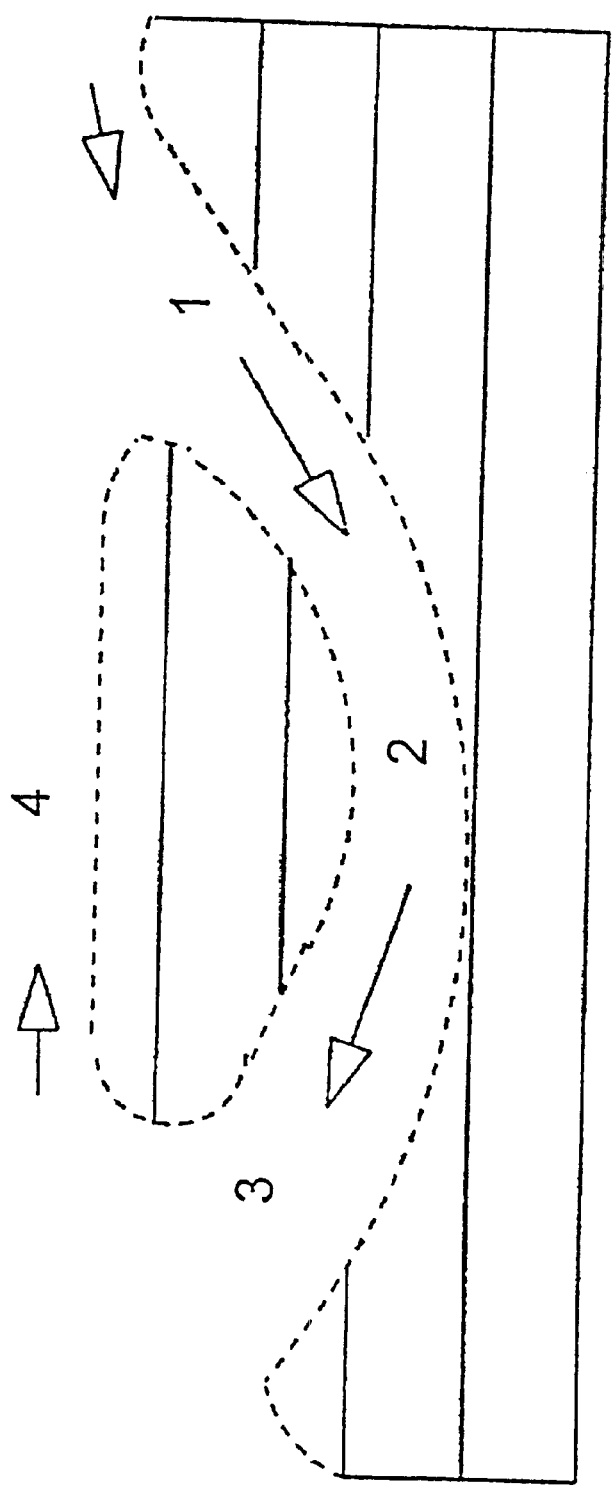
FIG. 7 schematically illustrates a re-entry path in myocardium tissue.

FIG. 7 schematically illustrates a re-entry path in myocardium tissue. Note that in a case when a unidirectional DGEW, generated in accordance with the present invention, could interrupt the re-entry loop, it would provide information about the exact location of the latter.

Figure 8:
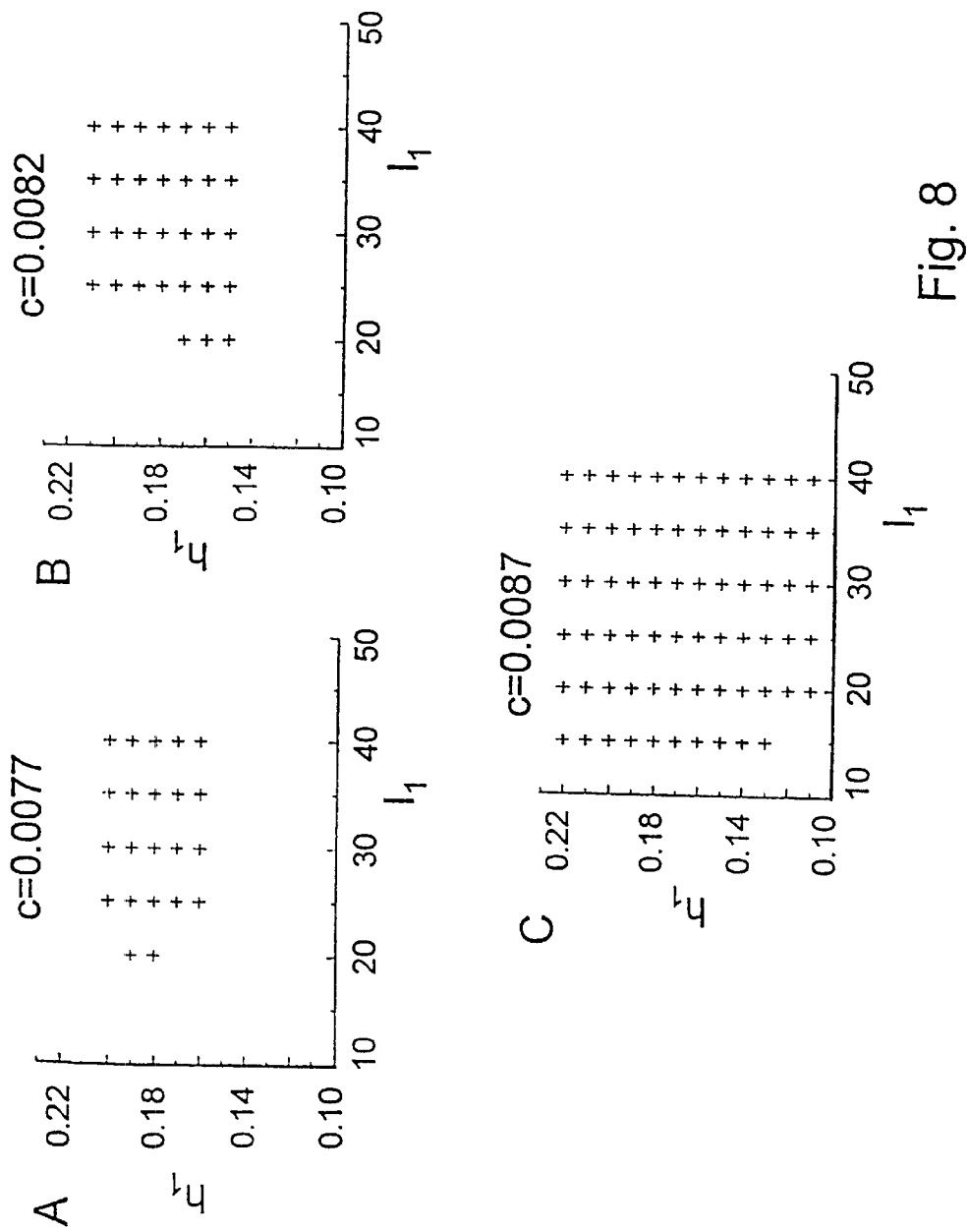
FIG. 8 schematically illustrates that unidirectional DGEWs could be obtained for several conditions, including those typical to an ischemic heart tissue.

FIG. 8 schematically illustrates the regions where unidirectional DGEWs are obtained for several conditions, which resemble ischemia. The results are shown in the $l_1$-$h_1$ domain for three different values of c, with other parameters held fixed: $\alpha=0.139$, d=2.54, D=1, $l_2=25$ and $h_2=0.4$. From the figure, it is clear that obtaining unidirectional DGEWs becomes easier with increasing value of c (i.e., the unidirectional DGEW region increases at more ischemic conditions).

According to a preferred embodiment of the invention, an easy and accurate localization for a re-entry path in an excitable tissue is found by using an invasive dual contact electrode, penetrate into the likely tissue, with the contacts spaced by the distance $l_3$. An asymmetric input impulse, such as the one shown in FIG. 1 above, is applied at the needles of the electrode and a corresponding unidirectional DGEW is generated. The generated unidirectional DGEW totally nulls the unwanted excitation wave oscillating in the re-entry path, if the unidirectional DGEW is generated and propagates in the main track of the re-entry path. If the unidirectional DGEW is generated and propagates in a secondary (or an auxiliary) track of the re-entry path, only temporary cancellation is achieved, followed by an eventual reset. In both cases, the total amount of energy delivered to the heart tissue is small (on the order of 10 mJ) and both pain and damage to the heart are avoided. Therefore, locations for re-entry paths are pinpointed whenever cancellation is obtained. Hence, after the re-entry path is identified and located, the re-entry region may be accurately ablated using any known technique, such as Radio-Frequency (RF) ablation.

According to a preferred embodiment of the invention, after identifying and locating re-entry paths in a patient's heart, such dual contact electrode is implanted in the patient's heart at that location. A unidirectional DGEW is generated by applying an input asymmetrical stimulus to the needles of the implanted electrode from an external or implanted circuitry, whenever actual or impending malignant cardiac arrhythmia is identified.

The above examples and descriptions have of course been provided only for the purpose of illustrations, and are not intended to limit the invention in any way. As will be appreciated by the skilled professional, the invention can be carried out in a great variety of ways, such as using non-rectangular excitation impulses, employing more than one technique than those described above, treating cardiac arrhythmias, all without exceeding the scope of the invention.

What is claimed is:

1. A device, which comprises means for canceling an unwanted excitation impulse that propagates in excitable tissue, comprising circuitry for generating a unidirectional Device-Generated Excitation Wave (DGEW) in said tissue.

2. A device according to claim 1, wherein the means for generating the unidirectional DGEW comprises first and second stimulation bipolar electrodes.

3. A device according to claim 2, wherein the first and second stimulation electrodes have the same polarity.

4. A device according to claim 2, wherein each stimulation electrode is fed by a power supply.

5. A device according to claim 2, wherein each stimulation electrode comprises a pair of conductive needles, the proximal end of which is connected to a contact of a power supply, operating in combination with a corresponding needle, connected to another contact of said power supply, thereby enabling current to flow between said conductive needles.

6. A device according to claim 2, further comprising a first needle and a second needle having opposite polarities, wherein the proximal end of each opposing polarity needle being connected to a corresponding power supply.

7. A device according to claim 4, comprising a first and a second power supply, each comprising a separate power source.

8. A device according to claim 4, comprising a first and a second power supply comprising a single power source with two separately controllable outputs.

9. A device according to claim 1, further comprising a first and a second control circuitry, respectively, for determining the required amplitude and duration of the voltage applied between the respective stimulation and opposing polarity electrodes.

10. A device according to claim 4, wherein the power supply that drives the first stimulation electrode is set to generate a first current impulse $S_1$, having a magnitude that is lower than the threshold level of the excitable tissue.

11. A device according to claim 4, wherein the power supply that drives the second stimulation electrode is set to generate a second current impulse $S_2$, having a magnitude that is higher than the threshold level of the excitable tissue.

12. A device according to claim 10, wherein the first and second current impulses are generated with a predetermined delay in respect to each other.

13. A device according to claim 12, wherein the delay between the two impulses is between −10 msec and +5 msec.

14. A device according to claim 9, further comprising timing circuitry for generating the desired delay.

15. A device according to claim 12, wherein the delay is set for compensating for fluctuations in distance between the respective stimulation electrodes.

16. A device according to claim 4, wherein the distance between the two stimulating electrodes is set so that the two stimulation impulses interact with each other only in one desired direction, while preventing interaction in the opposite direction.

17. A device according to claim 4, wherein the minimal distance between the two stimulation electrodes is adjusted to be approximately between 0.1 and 1.5 mm.

18. A device according to claim 2, wherein each stimulation electrode is provided with a needle, the distal end of which consists of an exposed metal cone.

19. A device according to claim 18, wherein the length of the distal end of the needle is approximately 100 $\mu$m, and the tip diameter is approximately 10 $\mu$m.

20. A device according to claim 11, wherein the original magnitude of the stimulus $S_2$ is between 1.0 and 1.5 times the threshold level of the excitable tissue.

21. A device according to claim 10, wherein the duration of each impulse is approximately 100 $\mu$sec.

22. A device according to claim 11, wherein the propagation direction of the impulse $S_1$ is switched by increasing the magnitude of the first impulse $S_2$ above the threshold level of the excitable tissue, and by decreasing the magnitude of the second impulse $S_1$ below the threshold level of the excitable tissue.

23. A device according to claim 14, further comprising detecting circuitry, linked to the first and second control circuitry of each stimulation electrode and to the timing circuitry, for detecting and pinpointing unwanted impulses in the excitable tissue which are above the threshold level.

24. A device according to claim 9, which is operated automatically whenever an unwanted excitation wave is detected.

25. A device according to claim 6, located outside of the excitable tissue and having electrodes implanted within said tissue.

26. A device according to claim 6, which is implantable in the excitable tissue.

27. A device according to claim 1, wherein the unwanted excitation impulse is malignant cardiac arrhythmias.

28. A device, for canceling an unwanted excitation impulse that propagates in excitable tissue, comprising:
   a) at least two stimulation bipolar electrodes, each of which comprising a pair of conductive needles, by which stimulating electrical energy is provided to said excitable tissue, said stimulating electrical energy being delivered to said excitable tissue so as to cause a unidirectional Device-Generated Excitation Wave in said excitable tissue, for canceling said unwanted excitation impulse; and
   b) at least one electrical energy source, connected to said stimulation electrodes, for providing, concurrently, or with a time delay in respect to each other, a different energy level to each of said stimulation electrodes.

29. A device according to claim 28, wherein the distance between the two stimulation electrodes is set so that the two stimulation impulses interact with each other only in one desired direction, while preventing interaction in the opposite direction.

30. A method for the medical treatment and suppression of malignant cardiac arrhythmias in patients, resulting from unwanted excitation waves generated and sustained in closed re-entry conductive paths in the heart of the patient, which comprises generating unidirectional excitation waves for interacting with said unwanted excitation waves and canceling them, and applying same to the heart tissue.

31. A method for medical treatment and suppression of malignant cardiac arrhythmias in patients, resulting from an unwanted excitation wave, the method comprising the steps of:
   a) generating in two different locations of the myocardium, low-energy, asymmetrical excitation impulses, the first impulse having magnitude below the threshold level of the myocardium tissue and the second impulse having magnitude above said threshold level;
   b) determining the distance between said two locations and the time of the generation of said impulses, so that a unidirectional Device Generated Excitation Wave is thereby generated; and
   c) applying said unidirectional excitation wave to the myocardial tissue to cancel an unwanted wave in its re-entry path.

32. A method according to claim 31, wherein one of the excitation impulses is generated with a delay in respect to the other one of the excitation impulses.

33. A method according to claim 31, wherein the two excitation impulses are generated concurrently.

34. A method according to claim 31, further comprising identifying the location of the re-entry path of the unwanted excitation wave from the direction of the DGEW, when this latter cancels said unwanted excitation wave, and delivering destructive energy to the identified location.

35. A method for the medical treatment and suppression of malignant cardiac arrhythmias in patients, comprising the steps of:
   a) generating, by means of a first bipolar electrode, a first impulse above the threshold that propagates opposite to the unwanted impulse, whereby when said first impulse meets said unwanted impulse, the two impulses cancel one another;
   b) generating, by means of a second bipolar electrode, a second impulse below the threshold, that propagates in the same direction as the unwanted impulse and delays;
   c) choosing the distance between said electrodes and the timing of the impulse generation in such a way that, the first electrode generates a third impulse above the threshold that propagates in a direction opposite to that of said first impulse threshold while the second electrode generates a fourth impulse below the threshold that propagates in a direction opposite to that of said second impulse, whereby said third and fourth impulse meet and their interaction generates a residual impulse that is below the threshold and decays; and
   d) provided that if said distance is small enough, no third and no fourth impulse are generated.

36. A device for canceling an unwanted excitation impulse that propagates in excitable tissue, comprising circuitry for generating a unidirectional Device-Generated Excitation Wave in said tissue and first and second bipolar electrodes for stimulating unidirectional pulses associated with said excitation wave, said circuitry capable of generating:
   a) a pair of first and second high-amplitude current impulses having an amplitude that is higher than the threshold level of the excitable tissue, said first high-amplitude impulse propagating in an opposite direction than said second high-amplitude impulse;
   b) a pair of first and second low-amplitude current impulses, having an amplitude that is lower than the threshold level of the excitable tissue, said first low-amplitude impulse propagating in an opposite direction than said second low-amplitude impulse; and
   c) a predetermined delay between the generation of said pair of low-amplitude impulses and said pair of high-amplitude impulses,
      said pair of high-amplitude impulses being generated by said first electrode and said pair of low-amplitude impulses being generated by said second electrode, wherein the distance between said first and second electrodes being selected so that a low-amplitude and a high-amplitude impulse interact with each other only in one desired direction, while preventing interaction in the opposite direction;
      said first low-amplitude impulse being capable of propagating in the same direction as an unwanted impulse and decaying, said first high-amplitude impulse being capable of propagating in the same direction as the unwanted impulse, and said second low-amplitude impulse being capable of propagating in the opposite direction as the unwanted impulse;
      said first high-amplitude impulse and said second low-amplitude impulse being capable of meeting and interacting, said interaction generating a residual impulse that is below the threshold level of the excitable tissue and decays;
      said second high-amplitude impulse being capable of propagating in a direction opposite to the unwanted impulse, whereby to meet said unwanted impulse, said second high-amplitude and said unwanted impulse cancel one another.

37. A device according to claim 36, wherein the first and second electrodes have the same polarity.

38. A device according to claim 36, wherein each electrode is fed by a power supply.

39. A device according to claim 38, comprising a first power supply and a second power supply, each comprising a separate power source.

40. A device according to claim 38, comprising a first power supply and a second power supply comprising a single power source with two separately controllable outputs.

41. A device according to claim 36, wherein each electrode comprises a pair of conductive needles, the proximal end of which is connected to a contact of a power supply, operating in combination with a corresponding needle, connected to another contact of said power supply, thereby enabling current to flow between said conductive needles.

42. A device according to claim 36, wherein each electrode comprises a first needle and a second needle having opposite polarities, and the proximal end of each opposing polarity needle being connected to a corresponding power supply.

43. A device according to claim 36, further comprising a first control circuitry and a second control circuitry for determining both the required amplitude and the required duration of voltage applied between the first and second electrodes, respectively.

44. A device according to claim 43, further comprising a timing circuitry for generating the predetermined delay.

45. A device according to claim 44, further comprising detecting circuitry, linked to the first and second control circuitry and to the timing circuitry, for detecting and pinpointing unwanted impulses in the excitable tissue which are above the threshold level.

46. A device according to claim 43, wherein the first and second control circuitry are operated automatically whenever an unwanted excitation wave is detected.

47. A device according to claim 36, wherein the predetermined delay between is between −10 msec and +5 msec.

48. A device according to claim 36, wherein the predetermined delay is selected to compensate for fluctuations in distance between the first and second electrodes.

49. A device according to claim 36, wherein the minimal distance between the two electrodes is adjusted to be approximately between 0.1 and 1.5 mm.

50. A device according to claim 36, wherein each electrode is provided with a needle, the distal end of which comprising an exposed metal cone.

51. A device according to claim 50, wherein the length of the distal end of the needle is approximately 100 μm and the tip diameter is approximately 10 μm.

52. A device according to claim 36, wherein the amplitude of each high-amplitude impulse is between 1.0 and 1.5 times the threshold level of the excitable tissue.

53. A device according to claim 36, wherein the duration of each impulse is approximately 100 μsec.

54. A device according to claim 36, wherein the propagation direction of the second high-amplitude impulse is controllable.

55. A device according to claim 36, wherein the circuitry for generating a Device Generated Excitation Wave is located outside of the excitable tissue and the first and second electrodes are implanted within said tissue.

56. A device according to claim 36, wherein the device is implantable in the excitable tissue.

57. A device according to claim 36, wherein the unwanted excitation impulse is malignant cardiac arrhythmias.

* * * * *